United States Patent
Kornek

(10) Patent No.: US 6,979,745 B2
(45) Date of Patent: Dec. 27, 2005

(54) PROCESS FOR PREPARING ORGANOSILICON COMPOUNDS CONTAINING ISOCYANATE GROUPS

(75) Inventor: Thomas Kornek, Burghausen (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 10/843,070

(22) Filed: May 11, 2004

(65) Prior Publication Data

US 2004/0249179 A1    Dec. 9, 2004

(30) Foreign Application Priority Data

Jun. 5, 2003 (DE) ................................ 103 25 608

(51) Int. Cl.$^7$ ................................. C07F 7/04

(52) U.S. Cl. .................................... 556/414

(58) Field of Search ......................... 556/414

(56) References Cited

U.S. PATENT DOCUMENTS

| 5,393,910 A | 2/1995 | Mui et al. |
| 6,008,396 A | 12/1999 | Sheridan et al. |

FOREIGN PATENT DOCUMENTS

| DE | 101 08 543 C1 | 4/2002 |
| EP | 0 870 769 A2 | 10/1998 |
| WO | WO 02/5002 A1 | 7/2002 |

OTHER PUBLICATIONS

Derwent Abstract corresp. to WO 02/50020 A1.
Derwent Abstract corresp. to DE 101 08 543 C1.

*Primary Examiner*—Samuel Barts
(74) *Attorney, Agent, or Firm*—Brooks Kushman P.C.

(57) ABSTRACT

Organosilicon compounds containing isocyanate groups and composed of units (Ia)

$$R_a(R^1O)_b X_c SiO_{(4-a-b-c)/2}, \quad (Ia)$$

are prepared by heating organosilicon compounds composed of units (Ib)

$$R_a(R^1O)_b Y_c SiO_{(4-a-b-c)/2}, \quad (Ib)$$

where
X is an SiC- or SiOC-bonded radical of the formula (IIa)

(IIa)  —(O)$_g$—Z—NCO,

Y is an SiC- or SiOC-bonded radical of the formula (IIb)

—(O)$_g$—Z—NH—C(O)OR$^2$ (IIb), g is 0 or 1, Z is a hydrocarbon spacer, R, R$^1$ and R$^2$ are optionally substituted hydrocarbon radicals, with the proviso that the organosilicon compounds of formula (Ib) possess a halide content of not more than 10,000 ppm by weight.

14 Claims, No Drawings

PROCESS FOR PREPARING ORGANOSILICON COMPOUNDS CONTAINING ISOCYANATE GROUPS

BACKGROUND OF THE INVENTION

1. Field of the Invention

The invention relates to a process for preparing organosilicon compounds containing isocyanate groups from organosilicon compounds containing carbamato groups and having a low halide content.

2. Background Art

Organosilicon compounds containing isocyanate groups can be employed in numerous applications, for example as adhesion promoters, coupling agents, crosslinkers or surface modifiers in sealants and adhesives, and as coatings additives, among others.

Various processes for synthesizing organosilicon compounds containing isocyanate groups have already been described, such as the reaction of trichlorosilane with allyl isocyanate under Pt catalysis. The latter process, however, is characterized by poor yields, and requires expensive unsaturated isocyanates. In a similar process, trialkoxysilanes are employed in lieu of trichlorosilanes. However, the use of trialkoxysilanes with their attendant high hazard potential, i.e. disproportionation during storage, formation of spontaneously flammable gases, toxicity, etc., imposes extremely high requirements on the process regime, thereby imposing additional restrictions on its economics.

Silicon-containing amines have also been reacted with phosgene in the presence of various HCl acceptors in order to obtain the corresponding isocyanate compounds. In view of the extraordinarily high toxicity of phosgene, costly and inconvenient safety measures are of course necessary in order to protect people and the environment.

There is also mention in the patent literature of thermal cleavage of organosilicon compounds containing carbamate groups at temperatures starting at about 300° C. e.g., U.S. Pat. No. 5,393,910 A. In these pyrolysis or thermolysis reactions the desired organosilicon compounds containing isocyanate groups are formed with the release of equimolar amounts of an alcohol. However, in practice, it has been found difficult to produce organosilicon compounds containing isocyanate groups in a continuous fashion by such methods, due to buildup of deposits in the thermolysis apparatus. The yields tend to be low, and the product is prone to discoloration.

SUMMARY OF THE INVENTION

It has now been surprisingly discovered that the low yields and the quantity of deposits in the thermolysis apparatus, as well as the amount of corrosion thereof, are related to the halide content of the carbamate to be thermolyzed to isocyanate. By providing a carbamate with a halide content less than 10,000 ppm, significant increases in both yield and product stability are possible.

DETAILED DESCRIPTION OF THE PREFERRED EMBODIMENTS

The invention provides a process for preparing organosilicon compounds which contain isocyanate groups and contain of units of the formula (Ia)

which involves heating organosilicon compounds containing units of formula (Ib)

where
X is an SiC— or SiOC-bonded radical of the formula (IIa)

$$-(O)_g-Z-NCO \qquad (IIa),$$

Y is an SiC- or SiOC-bonded radical of the formula (IIb)

g is 0 or 1,
Z is a divalent, unsubstituted or substituted ("optionally substituted") hydrocarbon radical which can be interrupted by O, S, N or P, R, $R^1$, and $R^2$ are each a monovalent, SiC-bonded, optionally substituted hydrocarbon radical which can be interrupted by O, S, N or P,
a and b are each independently 0, 1, 2 or 3, and
c is 0, 1, 2, 3 or 4,
with the provisos that the sum $a+b+c \leq 4$,
that the organosilicon compounds comprising units of the formula (Ia) contain at least one radical X, and
that the organosilicon compounds comprising units of the formula (Ib) contain at least one radical Y and also possess a halide content of not more than 10,000 ppm by weight.

It has been found that in preparing organosilicon compounds containing isocyanate groups, selectivity and yield of the process, the operating duration or "uptime" of the apparatus, for example a pyrolysis apparatus, as well as the utility of the desired products in their target applications, depend very heavily on the quality of the organosilicon compounds containing carbamate groups that are used. The aforesaid process parameters and associated qualities of the organosilicon products comprising units of the general formula (Ia) achieve an optimum, in particular, when the organosilicon compounds containing carbamate groups comprising units of the formula (Ib), are free from nonvaporizable byproducts, and in particular have halide contents of not more than 10,000 ppm, preferably not more than 5,000 ppm, more preferably not more than 1,000 ppm, and in particular not more than 100 ppm. The principal halides are chloride, bromide, and iodide.

The organosilicon compounds comprising units of the formula (Ia) that are prepared from low-halide organosilicon compounds comprising units of the formula (Ib) display superior properties, in some cases considerably so, over a wide range of applications as compared with otherwise similar organosilicon compounds containing isocyanate groups that are prepared from halide-rich carbamate-functional organosilicon compounds. Examples include adhesion of coating formulations and of adhesives and sealants to metallic surfaces. Moreover, low-halide organosilicon compounds comprising units of the general formula (Ia) are significantly more stable to chemical change on storage, for example changes in purity and color.

In the course of the process, alcohols of the general formula $R^2OH$ are eliminated from the radical Y of the general formula (IIb). $R^2$ is preferably a $C_1$–$C_6$ alkyl radical, more preferably a propyl, ethyl, or methyl radical.

The organosilicon compounds are preferably composed of 1 to 10 units, more preferably 1 to 3 units of the formulae (Ia) or (Ib). In particular the sum $a+b+c=4$; in other words, the organosilicon compounds are preferably silanes. Thus, the organosilicon compounds comprising units of the formula (Ia) preferably contain 1 to 10, in particular 1, 2 or 3 radicals X.

As spacers Z between the organosilicon groups or the isocyanate groups it is preferred to use linear or branched, saturated or unsaturated $C_1$–$C_6$ hydrocarbon groups. Preference is given to alkyl radicals, especially to linear alkyl radicals, and in particular, to methylene, ethylene, and propylene radicals.

Radicals R are preferably $C_1$–$C_{18}$ hydrocarbon groups. Preferred substituents on the radicals R are fluoro, chloro, and bromo. Halogen substituents covalently bound to radicals R are not counted when determining the halide content of the carbamate, the latter determined by methods well known to the art. Examples of radicals R are alkyl radicals such as the methyl, ethyl, n-propyl, isopropyl, n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, octadecyl radicals such as the n-octadecyl radical; alkenyl radicals such as the vinyl and allyl radicals, cycloalkyl radicals such as the cyclopentyl, cyclohexyl, cycloheptyl, and methylcyclohexyl radicals; aryl radicals such as the phenyl, naphthyl, anthryl, and phenanthryl radicals; alkaryl radicals such as the o-, m-, and p-tolyl radicals, xylyl radicals, and ethylphenyl radicals; aralkyl radicals such as the benzyl radical and the α- and β-phenylethyl radicals, preference being given to the methyl radical, ethyl radical, n-propyl radical, isopropyl radical, n-butyl radical, and the phenyl radical. Particularly preferred radicals R are the methyl radical and the phenyl radical.

Radicals $R^1$ are preferably $C_1$–$C_{10}$ hydrocarbon groups, especially $C_1$–$C_6$ alkyl groups. Particular preference is given to the propyl, ethyl, and methyl radicals.

In accordance with the inventive process, the organosilicon compounds comprising units of the formula (Ib) are preferably heated to a temperature of from 50 to 600° C., more preferably from 100 to 500° C., over a pressure range of 0.01–100 bar, more preferably 0.5–10 bar, and in particular, in the range 0.5–1.5 bar.

The process is generally characterized as a "pyrolysis" or "thermolysis" reaction, and can be carried out using any of the technical implementations known from the literature, such as baths of hot liquids or hot surfaces of metal, glass or ceramic materials, and also with reactors fabricated therefrom and in accordance with the state of the art, such as tube reactors, stirred reactors, loop reactors, cascade reactors, and so on. All of these processes can be carried out continuously or batchwise and in the presence or absence of catalysts.

One preferred apparatus for carrying out the process is, for example, an apparatus in which the carbamate-functional organosilicon compounds are introduced dropwise into hot liquids and the isocyanate-functional organosilicon compounds are removed by distillation. Also preferred are heatable tubular reactors of glass, metals, or other materials such as ceramics which are resistant under the thermolysis conditions, which, where appropriate, may be fitted with packings. Particularly preferred embodiments are packed and unpacked metallic tubes loaded with a catalytically active medium. Catalytic media which facilitate cleavage of carbamates to isocyanates are well known to those skilled in the carbamate thermolysis. Other preferred embodiments include stirred tank reactors, from which at appropriate temperatures the organosilicon compounds comprising units of the general formula (Ia) can be distilled out directly during the course of the pyrolysis or thermolysis reaction from the initially introduced organosilicon compounds comprising units of the general formula (Ib).

All of the above symbols in the above formulae have their definitions in each case independently of one another.

In the examples below, unless stated otherwise, all amounts and percentages are based on mass, all pressures are 0.10 MPA (abs.), and all temperatures are 20° C. For product isolation, the reaction mixtures were worked up by the conventional methods of liquid separation, i.e. continuous and discontinuous distillations.

COMPARATIVE EXAMPLE 100 g of N-[(3-(trimethoxysilyl)prop-1-yl)]-O-methylcarbamate with a chloride content of 2% were introduced dropwise into a steel pipe with a length of 1.00 m and an internal diameter of 0.05 m, which was heated at 500° C., until the starting product was no longer detectable in the emergent target product, the emergent product being analyzed by means of gas chromatography and $^{29}Si$ NMR spectroscopy. The crude product obtained was distilled through a 30 cm packed column (packing: 3 mm glass spirals), yielding 48.8 g of (3-isocyanatopropyl)trimethoxysilane. After just a few days of storage there appeared a distinct yellow coloration in conjunction with a corresponding decrease in the purity of the product.

After fifty experiments the steel tube was removed from the apparatus and inspected. In addition to black encrustations there were distinct traces of corrosion visible on the tube, making its further use impossible.

EXAMPLE 1

The comparative example was repeated with a steel pipe of the same construction but with the modification that, instead of the N-[(3-(trimethoxysilyl)prop-1-yl)]-O-methylcarbamate with a chloride content of 2%, a starting product with a chloride content of 0.5% was used. Distillative workup gave 61.2 g of (3-isocyanatopropyl)trimethoxysilane. After a few days of storage there appeared a slight yellow coloration in conjunction with a decrease in the purity of the product.

After fifty experiments the steel tube was removed from the apparatus and inspected. As well as slight crustations, very slight traces of corrosion were visible on the tube.

EXAMPLE 2

The comparative example was repeated with a steel pipe of the same construction but with the modification that, instead of the N-[(3-(trimethoxysilyl)prop-1-yl)]-O-methylcarbamate with a chloride content of 2%, a starting product with a chloride content of 100 ppm was used. Distillative workup gave 81.8 g of (3-isocyanatopropyl)trimethoxysilane.

After fifty experiments the steel tube was removed from the apparatus and inspected. Neither encrustations nor traces of corrosion were evident on the tube. Even after storage for several weeks the product showed no color changes at all.

What is claimed is:

1. A process for preparing organosilicon compounds which contain isocyanate groups and are comprised of units of the formula (Ia)

  (Ia), said process comprising heating organosilicon compounds comprised of units of the formula (Ib)

  (Ib), where
- X is an SiC- or SiOC-bonded radical of the general formula (IIa)

$$-(O)_g-Z-NCO \qquad (IIa),$$

- Y is an SiC- or SiOC-bonded radical of the general formula (IIb)

$$-(O)_g-Z-NH-C(O)OR^2 \qquad (IIb),$$

- g is 0 or 1,
- Z is a divalent, optionally substituted hydrocarbon radical spacer which can be interrupted by O, S, N or P,
- R, $R^1$, and $R^2$ are each independently a monovalent, SiC-bonded, optionally substituted hydrocarbon radical which can be interrupted by O, S, N or P,
- a and b are each independently 0, 1, 2 or 3, and
- c is 0, 1, 2, 3 or 4,
- with the provisos that the sum $a+b+c \leq 4$,
- that the organosilicon compounds comprising units of the formula (Ia) contain at least one radical X,
- that the organosilicon compounds comprising units of the formula (Ib) contain at least one radical Y, and
- that the organosilicon compounds comprising units of the formula (Ib) also contain halide, but in a content of not more than 10,000 ppm by weight.

2. The process of claim 1, in which $R^2$ is a $C_1$–$C_6$ alkyl radical.

3. The process of claim 1, in which the halides are selected from chloride, bromide, and iodide.

4. The process of claim 1, in which the spacer Z is a $C_1$–$C_6$ hydrocarbon group.

5. The process of claim 1, wherein said halide content is not more than 5000 ppm.

6. The process of claim 1, wherein said halide content is not more than 1000 ppm.

7. The process of claim 1, wherein said halide content is not more than 100 ppm.

8. The process of claim 7, in which $R^2$ is a $C_1$–$C_6$ alkyl radical.

9. The process of claim 7, in which the halides are selected from chloride, bromide, and iodide.

10. The process of claim 7, in which the spacer Z is a $C_1$–$C_6$ hydrocarbon group.

11. The process of claim 2, wherein the halide content of the organosilicon compound(s) of the formula (Ib) is less than 5000 ppm.

12. The process of claim 2, wherein the halide content of the organosilicon compound(s) of the formula (Ib) is less than 1000 ppm.

13. The process of claim 2, wherein the halide content of the organosilicon compound(s) of the formula (Ib) is less than 100 ppm.

14. The process of claim 1, wherein the halide content of the organosilicon compound(s) of the formula (Ib) is from 100 ppm to 5000 ppm.

* * * * *